United States Patent
Von Arx et al.

(10) Patent No.: US 8,755,899 B2
(45) Date of Patent: *Jun. 17, 2014

(54) HELICAL ANTENNA FOR AN IMPLANTABLE MEDICAL DEVICE

(75) Inventors: Jeffrey A. Von Arx, Minneapolis, MN (US); William R. Mass, Maple Grove, MN (US); Scott T. Mazar, Inver Grove Heights, MN (US); Mark D. Amundson, Cambridge, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1149 days.

This patent is subject to a terminal disclaimer.

(21) Appl. No.: 12/359,739

(22) Filed: Jan. 26, 2009

(65) Prior Publication Data

US 2009/0192574 A1 Jul. 30, 2009

Related U.S. Application Data

(63) Continuation of application No. 10/800,596, filed on Mar. 15, 2004, now Pat. No. 7,483,752, which is a continuation of application No. 09/798,249, filed on Mar. 2, 2001, now Pat. No. 6,708,065.

(51) Int. Cl.
*A61N 1/02* (2006.01)
*A61N 1/372* (2006.01)

(52) U.S. Cl.
CPC .................................. *A61N 1/37229* (2013.01)
USPC ........................................................... 607/60

(58) Field of Classification Search
None
See application file for complete search history.

(56) References Cited

U.S. PATENT DOCUMENTS

| | | | |
|---|---|---|---|
| 3,667,477 A | 6/1972 | Susset et al. |
| 3,718,909 A | 2/1973 | Greatbatch |
| 3,830,242 A | 8/1974 | Greatbatch |
| 4,230,128 A | 10/1980 | Aramayo |
| 4,262,632 A | 4/1981 | Hanton et al. |
| 4,341,982 A | 7/1982 | Lahti et al. |
| 4,441,498 A | 4/1984 | Nordling |
| 4,519,401 A | 5/1985 | Ko et al. |
| 4,542,535 A | 9/1985 | Bates et al. |
| 4,556,063 A | 12/1985 | Thompson et al. |
| 4,562,841 A | 1/1986 | Brockway et al. |
| 4,580,950 A | 4/1986 | Sumikawa et al. |
| 4,634,294 A | 1/1987 | Christol et al. |

(Continued)

FOREIGN PATENT DOCUMENTS

| | | |
|---|---|---|
| EP | 0168640 A2 | 1/1986 |
| EP | 1050265 A2 | 11/2000 |

(Continued)

OTHER PUBLICATIONS

"U.S. Appl. No. 09/798,249, Non-Final Office Action mailed Mar. 28, 2003", 7 pgs.

(Continued)

*Primary Examiner* — Kennedy Schaetzle
(74) *Attorney, Agent, or Firm* — Schwegman, Lundberg & Woessner, P.A.

(57) ABSTRACT

An apparatus and method for enabling far-field radio-frequency communications with an implantable medical device in which an antenna is embedded within a dielectric compartment of the device. A helical antenna may be employed to save space while still permitting far-field telemetry over a desired range of frequencies.

14 Claims, 4 Drawing Sheets

(56) References Cited

U.S. PATENT DOCUMENTS

| | | | |
|---|---|---|---|
| 4,803,987 A | 2/1989 | Calfee et al. |
| 4,944,299 A | 7/1990 | Silvian |
| 5,025,808 A | 6/1991 | Hafner |
| 5,058,581 A | 10/1991 | Silvian |
| 5,089,019 A | 2/1992 | Grandjean |
| 5,109,853 A | 5/1992 | Taicher et al. |
| 5,113,869 A | 5/1992 | Nappholz et al. |
| 5,118,825 A | 6/1992 | Wu |
| 5,127,404 A | 7/1992 | Wyborny et al. |
| 5,314,453 A | 5/1994 | Jeutter |
| 5,336,245 A | 8/1994 | Adams Theodore P. et al. |
| 5,337,756 A | 8/1994 | Barbier et al. |
| 5,342,408 A | 8/1994 | deCoriolis et al. |
| 5,385,578 A | 1/1995 | Bush et al. |
| 5,486,200 A | 1/1996 | Lindemans |
| 5,516,285 A | 5/1996 | Yacker et al. |
| 5,534,019 A | 7/1996 | Paspa |
| 5,535,752 A | 7/1996 | Halperin et al. |
| 5,556,421 A | 9/1996 | Prutchi et al. |
| 5,562,713 A | 10/1996 | Silvian |
| 5,579,876 A | 12/1996 | Adrian et al. |
| 5,593,430 A | 1/1997 | Renger |
| 5,598,847 A | 2/1997 | Renger |
| 5,650,759 A | 7/1997 | Hittman et al. |
| 5,683,432 A | 11/1997 | Goedeke et al. |
| 5,697,958 A | 12/1997 | Paul et al. |
| 5,735,887 A | 4/1998 | Barreras, Sr. et al. |
| 5,749,912 A | 5/1998 | Zhang et al. |
| 5,755,748 A * | 5/1998 | Borza ............... 607/61 |
| 5,766,232 A | 6/1998 | Grevious et al. |
| 5,784,032 A | 7/1998 | Johnston et al. |
| 5,807,397 A | 9/1998 | Barreras |
| 5,833,603 A | 11/1998 | Kovacs et al. |
| 5,861,019 A | 1/1999 | Sun et al. |
| 5,862,803 A | 1/1999 | Besson et al. |
| 5,876,331 A | 3/1999 | Wu |
| 5,904,708 A | 5/1999 | Goedeke |
| 5,919,210 A | 7/1999 | Lurie et al. |
| 5,957,854 A | 9/1999 | Besson et al. |
| 5,958,645 A | 9/1999 | Hirose et al. |
| 6,009,350 A | 12/1999 | Renken |
| 6,115,583 A | 9/2000 | Brummer et al. |
| 6,115,634 A * | 9/2000 | Donders et al. ............ 607/32 |
| 6,115,636 A | 9/2000 | Ryan |
| 6,116,636 A | 9/2000 | Bianchi Bazzi |
| 6,169,925 B1 | 1/2001 | Villaseca et al. |
| 6,205,358 B1 | 3/2001 | Haeg et al. |
| 6,240,317 B1 | 5/2001 | Villaseca et al. |
| 6,263,246 B1 | 7/2001 | Goedeke et al. |
| 6,275,737 B1 | 8/2001 | Mann |
| 6,309,350 B1 | 10/2001 | VanTassel et al. |
| 6,329,920 B1 | 12/2001 | Morrison et al. |
| 6,388,628 B1 | 5/2002 | Dettloff et al. |
| 6,392,610 B1 | 5/2002 | Braun et al. |
| 6,416,471 B1 | 7/2002 | Kumar et al. |
| 6,427,088 B1 | 7/2002 | Bowman, IV et al. |
| 6,434,429 B1 | 8/2002 | Kraus et al. |
| 6,456,256 B1 | 9/2002 | Amundson et al. |
| 6,470,215 B1 | 10/2002 | Kraus et al. |
| 6,505,072 B1 | 1/2003 | Linder et al. |
| 6,505,077 B1 | 1/2003 | Kast et al. |
| 6,531,982 B1 | 3/2003 | White et al. |
| 6,535,766 B1 | 3/2003 | Thompson et al. |
| 6,561,975 B1 | 5/2003 | Pool et al. |
| 6,574,508 B2 | 6/2003 | Zaouali et al. |
| 6,574,509 B2 | 6/2003 | Kraus et al. |
| 6,574,510 B2 | 6/2003 | Von Arx et al. |
| 6,592,518 B2 | 7/2003 | Denker et al. |
| 6,614,406 B2 | 9/2003 | Amundson et al. |
| 6,622,043 B1 | 9/2003 | Kraus et al. |
| 6,675,045 B2 | 1/2004 | Mass et al. |
| 6,687,546 B2 | 2/2004 | Lebel et al. |
| 6,708,065 B2 | 3/2004 | Von Arx et al. |
| 6,721,602 B2 | 4/2004 | Engmark et al. |
| 6,766,200 B2 | 7/2004 | Cox |
| 6,804,561 B2 | 10/2004 | Stover |
| 6,809,701 B2 | 10/2004 | Amundson et al. |
| 6,868,288 B2 | 3/2005 | Thompson |
| 7,016,733 B2 | 3/2006 | Dublin et al. |
| 7,072,718 B2 | 7/2006 | Von Arx et al. |
| 7,103,413 B2 | 9/2006 | Swanson et al. |
| 7,149,578 B2 | 12/2006 | Edvardsson |
| 7,289,855 B2 | 10/2007 | Nghiem et al. |
| 7,309,262 B2 | 12/2007 | Zart et al. |
| 7,313,441 B2 | 12/2007 | Mass et al. |
| 7,317,946 B2 | 1/2008 | Twetan et al. |
| 7,319,901 B2 | 1/2008 | Dublin et al. |
| 7,363,087 B2 | 4/2008 | Nghiem et al. |
| 7,483,752 B2 | 1/2009 | Von Arx et al. |
| 7,613,522 B2 | 11/2009 | Christman et al. |
| 7,720,544 B2 | 5/2010 | Christman et al. |
| 8,352,044 B2 | 1/2013 | Christman et al. |
| 8,369,961 B2 | 2/2013 | Christman et al. |
| 2001/0034543 A1 | 10/2001 | Haeg |
| 2001/0047125 A1 | 11/2001 | Quy |
| 2002/0037756 A1 | 3/2002 | Jacobs et al. |
| 2002/0045920 A1 | 4/2002 | Thompson |
| 2002/0065539 A1 | 5/2002 | Von Arx et al. |
| 2002/0095195 A1 | 7/2002 | Mass et al. |
| 2002/0123776 A1 | 9/2002 | Von Arx et al. |
| 2003/0023175 A1 | 1/2003 | Arzbaecher et al. |
| 2003/0025645 A1 | 2/2003 | Amundson et al. |
| 2003/0028902 A1 | 2/2003 | Cubley et al. |
| 2003/0040779 A1 | 2/2003 | Engmark et al. |
| 2003/0083719 A1 | 5/2003 | Shankar et al. |
| 2003/0195589 A1 | 10/2003 | Von Arx et al. |
| 2004/0027306 A1 | 2/2004 | Amundson et al. |
| 2004/0046637 A1 | 3/2004 | Wesby Van Swaay |
| 2004/0060011 A1 | 3/2004 | Nitta et al. |
| 2004/0123667 A1 | 7/2004 | McGrath |
| 2004/0147969 A1 | 7/2004 | Mann et al. |
| 2004/0147974 A1 | 7/2004 | Engmark et al. |
| 2004/0152953 A1 | 8/2004 | Goedeke |
| 2004/0167580 A1 | 8/2004 | Mann et al. |
| 2004/0176811 A1 | 9/2004 | Von Arx et al. |
| 2004/0215958 A1 | 10/2004 | Ellis et al. |
| 2005/0027175 A1 | 2/2005 | Yang |
| 2005/0027192 A1 | 2/2005 | Govari et al. |
| 2005/0113886 A1 | 5/2005 | Fischell et al. |
| 2005/0203583 A1 | 9/2005 | Twetan et al. |
| 2005/0203584 A1 | 9/2005 | Twetan et al. |
| 2005/0222633 A1 | 10/2005 | Edvardsson |
| 2006/0089682 A1 | 4/2006 | Kronich et al. |
| 2006/0224206 A1 | 10/2006 | Dublin et al. |
| 2006/0247711 A1 | 11/2006 | Verhoef et al. |
| 2006/0247712 A1 | 11/2006 | Fuller et al. |
| 2007/0142829 A1 | 6/2007 | Ahn et al. |
| 2007/0179554 A1 | 8/2007 | Iyer et al. |
| 2007/0222697 A1 | 9/2007 | Caimi et al. |
| 2007/0260294 A1 | 11/2007 | Schulman et al. |
| 2007/0288065 A1 | 12/2007 | Christman et al. |
| 2007/0288066 A1 | 12/2007 | Christman et al. |
| 2008/0021522 A1 | 1/2008 | Verhoef et al. |
| 2008/0039898 A1 | 2/2008 | Lim et al. |
| 2010/0016925 A1 | 1/2010 | Christman et al. |
| 2010/0204759 A1 | 8/2010 | Christman et al. |

FOREIGN PATENT DOCUMENTS

| | | |
|---|---|---|
| EP | 1393672 A1 | 3/2004 |
| EP | 1537895 A1 | 6/2005 |
| EP | 1362614 B1 | 3/2008 |
| WO | WO-98/48895 A1 | 11/1998 |
| WO | WO-00/62664 A1 | 10/2000 |
| WO | WO-01/80731 A1 | 11/2001 |
| WO | WO-01/91428 A2 | 11/2001 |
| WO | WO-02/31909 A1 | 4/2002 |
| WO | WO-02/089667 A1 | 11/2002 |
| WO | WO-03/053515 A1 | 7/2003 |
| WO | WO-2004/066834 A1 | 8/2004 |

(56) References Cited

FOREIGN PATENT DOCUMENTS

| WO | WO-2005/123186 A1 | 12/2005 |
|----|-------------------|---------|
| WO | WO-2006/060750 A1 | 6/2006 |
| WO | WO-2006/131302 A1 | 12/2006 |

OTHER PUBLICATIONS

"U.S. Appl. No. 09/798,249, Notice of Allowance mailed Oct. 21, 2003", 5 pgs.

"U.S. Appl. No. 09/798,249, Response filed Jul. 28, 2003 to Non Final Office Action mailed Mar. 28, 2003", 8 pgs.

"U.S. Appl. No. 09/921,653, Notice of Allowance mailed May 7, 2002", 6 pgs.

"U.S. Appl. No. 10/194,401, Non-Final Office Action mailed Jun. 29, 2005", 4 pgs.

"U.S. Appl. No. 10/194,401, Notice of Allowance mailed Mar. 6, 2006", 4 pgs.

"U.S. Appl. No. 10/194,401, Amendment Under 37 CFR 1.312 filed Apr. 11, 2006", 5 pgs.

"U.S. Appl. No. 10/194,401, Final Office Action mailed Dec. 28, 2005", 8 pgs.

"U.S. Appl. No. 10/194,401, Response filed Feb. 28, 2006 to Final Office Action mailed Dec. 28, 2005", 7 pgs.

"U.S. Appl. No. 10/194,401, Response filed Sep. 29, 2005 to Non Final Office Action mailed Jun. 29, 2005", 7 pgs.

"U.S. Appl. No. 10/252,494, Notice of Allowance mailed Mar. 25, 2003", 5 pgs.

"U.S. Appl. No. 10/252,494, Non-Final Office Action mailed Jan. 30, 2003", 4 pgs.

"U.S. Appl. No. 10/252,494, Response filed Mar. 5, 2003 to Non-Final Office Action mailed Jan. 30, 2003", 6 pgs.

"U.S. Appl. No. 10/634,233, Notice of Allowance mailed Jun. 16, 2004", 6 pgs.

"U.S. Appl. No. 10/800,596, Amendment and Response filed Jun. 7, 2007 to Final Office Action mailed Mar. 7, 2007", 8 pgs.

"U.S. Appl. No. 10/800,596, Final Office Action mailed Dec. 4, 2007", 4 pgs.

"U.S. Appl. No. 10/800,596, Final Office Action mailed Mar. 7, 2007", 7 pgs.

"U.S. Appl. No. 10/800,596, Non-Final Office Action mailed Mar. 3, 2008", 9 pgs.

"U.S. Appl. No. 10/800,596, Non-Final Office Action mailed Jun. 28, 2007", 6 pgs.

"U.S. Appl. No. 10/800,596, Notice of Allowance mailed Sep. 17, 2008", 4 pgs.

"U.S. Appl. No. 10/800,596, Response filed Feb. 4, 2008 to Final Office Action mailed Dec. 4, 2007", 6 pgs.

"U.S. Appl. No. 10/800,596, Response filed Jun. 3, 2008 to Non-Final Office Action mailed Mar. 3, 2008", 8 pgs.

"U.S. Appl. No. 10/800,596, Response filed Sep. 28, 2007 to Non-Final Office Action mailed Jun. 28, 2007", 8 pgs.

"U.S. Appl. No. 11/423,254, Restriction Requirement mailed Mar. 31, 2009", 9 pgs.

"U.S. Appl. No. 11/423,254, Response filed Apr. 30, 2009 to Restriction Requirement mailed Mar. 31, 2009", 11 pgs.

"U.S. Appl. No. 11/423,254, Non-Final Office Action mailed Jul. 28, 2009", 10 pgs.

"U.S. Appl. No. 11/423,262, Non-Final Office Action mailed Dec. 24, 2008", 9 pgs.

"U.S. Appl. No. 11/423,262, Response filed Mar. 24, 2009 to Non Final Office Action mailed Dec. 24, 2008", 9 pgs.

"U.S. Appl. No. 11/423,262, Notice of Allowance mailed Jun. 23, 2009", 7 pgs.

Christman, Timothy J, et al., "Multi-Antenna for an Implantable Medical Device", U.S. Appl. No. 11/423,262, filed Jun. 9, 2006, 24 pgs.

Christman, Timothy J, et al., "Systems for Enabling Telemetry in an Implantable Medical Device", U.S. Appl. No. 11/423,254, filed Jun. 9, 2006, 22 pgs.

Karacolak, T., et al., "Design of a Dual-Band Implantable Antenna and Development of Skin Mimicking Gels for Continuous Glucose Monitoring", IEEE Transactions on Microwave Theory and Techniques, 56(4), (Apr. 2008), 1001-1008.

"U.S. Appl. No. 11/423,254, Notice of Allowance mailed Dec. 31, 2009", 7 pgs.

"U.S. Appl. No. 11/423,254, Response filed Oct. 28, 2009 to Non Final Office Action mailed Jul. 28, 2009", 14 pgs.

"U.S. Appl. No. 12/565,482, Notice of Allowance mailed Oct. 2, 2012", 7 pgs.

"U.S. Appl. No. 12/565,482, Response filed Sep. 21, 2012 to Final Office Action mailed Jun. 21, 2012", 10 pgs.

"U.S. Appl. No. 12/762,086, Response filed Aug. 15, 2012 to Final Office Action mailed May 15, 2012", 9 pgs.

"U.S. Appl. No. 12/762,086, Notice of Allowance mailed Aug. 27, 2012", 7 pgs.

* cited by examiner

HELICAL ANTENNA FOR AN IMPLANTABLE MEDICAL DEVICE

CROSS-REFERENCE TO RELATED APPLICATION(S)

This application is a continuation of U.S. patent application Ser. No. 10/800,596, filed on Mar. 15, 2004, now issued as U.S. Pat. No. 7,483,752, which is a continuation of U.S. patent application Ser. No. 09/798,249, filed on Mar. 2, 2001, now issued as U.S. Pat. No. 6,708,065, the specifications of which are incorporated herein by reference.

FIELD OF THE INVENTION

This invention pertains to implantable medical devices such as cardiac pacemakers and implantable cardioverter/defibrillators. In particular, the invention relates to an apparatus and method for enabling radio-frequency telemetry in such devices.

BACKGROUND

Implantable medical devices, including cardiac rhythm management devices such as pacemakers and implantable cardioverter/defibrillators, typically have the capability to communicate data with a device called an external programmer via a radio-frequency telemetry link. A clinician may use such an external programmer to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data which may typically be telemetered from an implantable device are various operating parameters and physiological data, the latter either collected in real-time or stored from previous monitoring operations.

Telemetry systems for implantable medical devices utilize radio-frequency energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand which can be positioned in proximity to the implanted device. The implantable device also generates and receives the radio signal by means of an antenna, typically formed by a wire coil wrapped around the periphery of the inside of the device casing.

In previous telemetry systems, the implantable device and the external programmer communicate by generating and sensing a modulated electromagnetic field in the near-field region with the antennas of the respective devices inductively coupled together. The wand must therefore be in close proximity to the implantable device, typically within a few inches, in order for communications to take place. This requirement is an inconvenience for a clinician and limits the situations in which telemetry can take place.

SUMMARY OF THE INVENTION

The present invention is an apparatus and method for enabling communications with an implantable medical device utilizing far-field electromagnetic radiation. Using far-field radiation allows communications over much greater distances than with inductively coupled antennas. Efficient emission and reception of far-field energy in a desirable frequency range, however, requires an antenna structure with certain minimum dimensions. An objective of the present invention is to provide such an antenna structure that does not complicate the implantation procedure, does not interfere with the device at its implanted site, and is resistant to breakage or deformation due to body movements.

In accordance with the invention, a wire or other type of antenna is embedded in dielectric material and located within the unshielded header of an implantable device where therapy leads are routed via feedthroughs to circuitry within the device housing. Alternatively, the embedded antenna is located within an unshielded housing portion of an implantable device such as a dielectric pocket or window adjacent to the rest of the housing. The antenna is connected to circuitry in order to enable the transmitting and receiving of far-field radio-frequency radiation modulated with telemetry data. By containing the antenna in this manner, the antenna is protected from bending or breakage and requires no special implantation procedure.

The dimensions of an antenna structure contained within a device header or housing portion are constrained by the size of those compartments, and it is desirable for implantable medical devices to be as small as possible. In another aspect of the invention, a helically wound dipole or monopole antenna is employed. A helical antenna is especially advantageous for this purpose because it has a longer effective electrical length than a similarly dimensioned straight wire dipole or monopole antenna. The antenna may also be tuned with a tuning circuit that optimizes its impedance for a particular frequency.

DETAILED DESCRIPTION

Figure 1A:
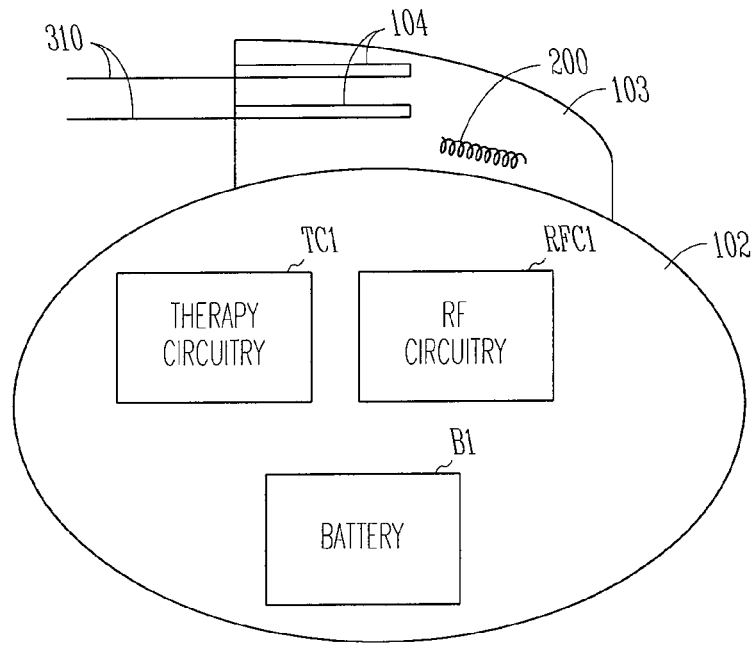
FIGS. 1A through 1D illustrate different methods for compartmentalizing an embedded antenna within an implantable medical device.

As noted above, conventional radio-frequency (RF) telemetry systems used for implantable medical devices such as cardiac pacemakers utilize inductive coupling between the antennas of the implantable device and an external programmer in order to transmit and receive RF signals. Because the induction field produced by a transmitting antenna falls off rapidly with distance, such systems require close proximity between the implantable device and a wand antenna of the external programmer in order to work properly, usually on the order of a few inches. The present invention, on the other hand, is an apparatus and method for enabling telemetry with an implantable medical device utilizing far-field radiation. Communication using far-field radiation can take place over much greater distances which makes it more convenient to use an external programmer. Also, the increased communication range makes possible other applications of the telemetry system such as remote monitoring of patients and communication with other types of external devices.

A time-varying electrical current flowing in an antenna produces a corresponding electromagnetic field configuration that propagates through space in the form of electromagnetic waves. The total field configuration produced by an antenna can be decomposed into a far-field component, where the magnitudes of the electric and magnetic fields vary inversely with distance from the antenna, and a near-field component with field magnitudes varying inversely with higher powers of the distance. The field configuration in the immediate vicinity of the antenna is primarily due to the near-field component, also known as the induction field, while the field configuration at greater distances is due solely to the far-field component, also known as the radiation field. The near-field is a reactive field in which energy is stored and retrieved but results in no net energy outflow from the antenna unless a load is present in the field, coupled either inductively or capacitively to the antenna. The far-field, on the other hand, is a radiating field that carries energy away from the antenna regardless of the presence of a load in the field. This energy loss appears to a circuit driving the antenna as a resistive impedance which is known as the radiation resistance. If the frequency of the RF energy used to drive an antenna is such that the wavelength of electromagnetic waves propagating therein is much greater than the length of the antenna, a negligible far-field component is produced. In order for a substantial portion of the energy delivered to the antenna to be emitted as far-field radiation, the wavelength of the driving signal should not be very much larger than the length of the antenna.

An antenna most efficiently radiates energy if the length of the antenna is an integral number of half-wavelengths of the driving signal. A dipole antenna, for example, is a center-driven conductor which has a length equal to half the wavelength of the driving signal. Such a dipole antenna can be made of two lengths of metal arranged end to end with the cable from a transmitter/receiver feeding each length of the dipole in the middle. An efficiently radiating resonant structure is formed if each length of metal in the dipole is a quarter-wavelength long, so that the combined length of the dipole from end to end is a half-wavelength. A shorter antenna can produce a similar field configuration by utilizing a ground plane to reflect electromagnetic waves emitted by the antenna and thereby produce an image field. A monopole antenna is a conductor with a length equal to one-quarter the wavelength of the driving signal situated with respect to a reflecting ground plane so that the total emitted and reflected field configuration resembles that of the dipole antenna. As will be discussed below, an antenna tuning circuit may also be used to alter the effective electrical length of an antenna by loading it with capacitance or inductance.

One way of implementing far-field telemetry in an implantable medical device is to use an antenna that extends from the device housing. The device housing is metallic and forms an electrically shielded compartment for electronic circuitry that provides particular functionality to the device such as cardiac rhythm management, physiological monitoring, drug delivery, or neuromuscular stimulation. The housing also contains circuitry for transmitting and receiving RF communications. The antenna could then take the form of a conductor covered by insulation that extends from the housing and is electrically connected to the RF transmitter/receiver within the housing. The antenna could be any conductive structure capable of efficiently radiating electromagnetic energy well-known to those of skill in the art such as a rod, a wire, a patch, or a loop.

An external wire antenna for an implantable medical device capable of emitting far-field radiation, however, may require special implantation procedures and may also be broken or deformed as a patient moves resulting in de-tuning. In accordance with the present invention, therefore, an antenna for an implantable medical device is embedded in a dielectric and contained within a compartment of the implantable device. As described below with respect to specific embodiments, the compartment may take the form of a specialized dielectric pocket or window integral to the device housing or may be the unshielded device header.

As noted above, two common types of antennas are wire dipole and monopole antennas. If a substantial portion of the RF energy delivered to the antenna to be emitted as far-field radiation, the length of the antenna should not be very much shorter than one-quarter of the wavelength of the RF carrier signal provided by the RF transmitter. For implantable medical device applications, carrier frequencies between 300 MHz and 1 GHz are most desirable. For example, the carrier signal may be selected to be 1 gigahertz, which corresponds to a wavelength of approximately 32 cm. A half-wavelength dipole antenna would optimally be approximately 16 cm long, and a quarter-wavelength monopole antenna would optimally have a length approximately 8 cm with the housing 101 serving as a ground plane. If it is desired to use a lower frequency carrier, even longer antennas must be used. Depending upon the size of the implantable device, it may or may not be convenient to embed a wire antenna in a compartment of the device as described below. For reasons of patient comfort, however, it is desirable for implanted devices to be as small as possible, and this constrains the length of the antenna that can be used if it is to be embedded in a compartment.

In another aspect of the invention, therefore, a helical antenna is employed to transmit and receive RF signals. Such an antenna is formed by helically coiling a length of wire or other conductor along a particular axis. If the circumference of the individual helices is small in comparison to the wavelength of the driving or received signal, the radiation pattern of the helical antenna is approximately the same as either a dipole antenna or a monopole antenna if a ground plane is present. A helical dipole or monopole antenna may be formed by coiling a length of wire corresponding to just over one-half wavelength or one-quarter wavelength of the carrier frequency. Owing to the coiling of the wire, the resulting helical antenna is physically shorter than the monopole or dipole antenna formed from the straight piece of wire. The effective electrical length of a the helical antenna, however, is even longer than that owing to the added inductance of the coil and turn-to-turn capacitance which reduces the resonance frequency from that of the corresponding straight wire antenna. A helical antenna thus provides a shortened, space-saving monopole or dipole antenna that behaves electrically like a much longer antenna.

FIGS. 1A through 1D show different embodiments of an exemplary implantable cardiac rhythm management device with a compartmentalized helical antenna 200 suitable for radiating and receiving far-field electromagnetic radiation. The device housing 102 is metallic and contains therapy circuitry TC1 for providing particular functionality to the device such as cardiac rhythm management, physiological monitoring, drug delivery, or neuromuscular stimulation as well as circuitry RFC1 for providing RF communications. A battery B1 is used to supply power to the electronic circuitry within the housing. One or more therapy leads 310 are connected to the therapy circuitry contained within the housing by means of a header 103 with feedthroughs located therein for routing the therapy leads to the appropriate internal components.

Figure 1B:
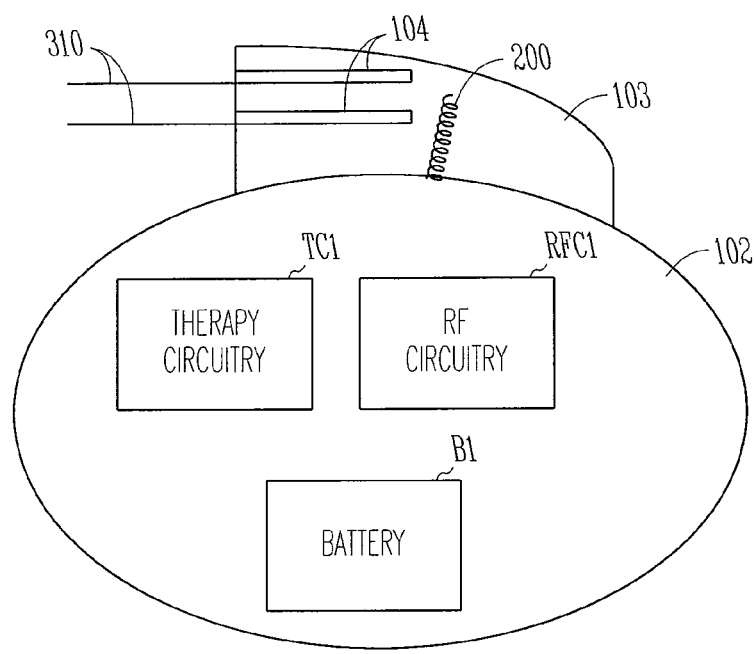

In FIGS. 1A and 1B, the helical antenna 103 is shown as being embedded within the header 103. The header 103 is a solid block structure made from a synthetic polymer that has feedthroughs therein for routing electrical connectors between the therapy leads 310 and the therapy circuitry TC1, with the proximal ends of the therapy leads being inserted into bores 104. The polymer material of the header is a dielectric that allows transmission and receipt of RF energy while also providing a rigid covering that protects the antenna from bodily fluids and prevents breakage or bending of the antenna. Putting the antenna into the header in this manner also involves no special implantation techniques and leaves the physical profile of the device housing unaltered. FIG. 1A shows the antenna 200 positioned roughly parallel to the surface of the device housing. In this configuration the helically coiled wire acts as a dipole antenna with a particular effective electrical length. FIG. 1B shows an alternative embodiment in which the antenna 200 is positioned within the header perpendicular to the surface of the device housing. In this configuration, the conductive device housing 102 acts as a ground plane so that the helical coil acts as a monopole antenna and behaves with an electrical length twice that of a similarly dimensioned dipole antenna.

Figure 1C:
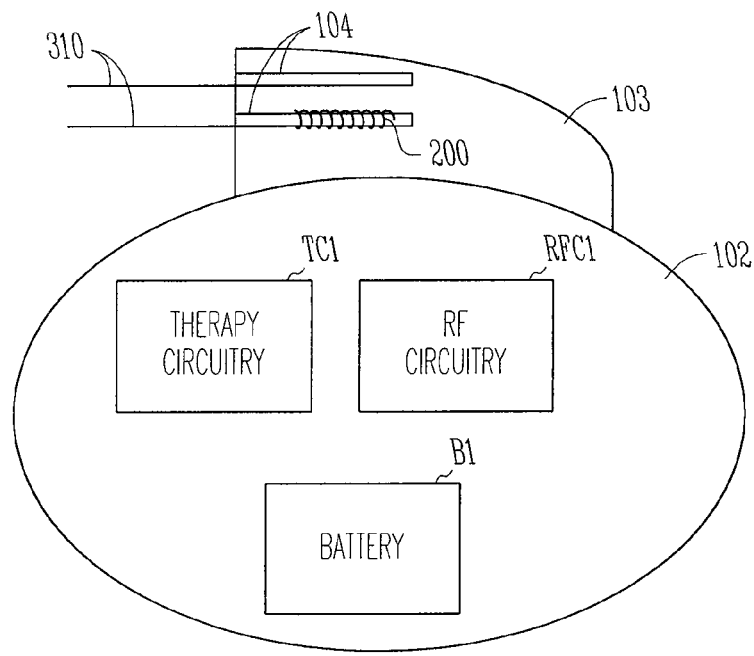

FIG. 1C illustrates an alternative location for embedding the antenna within the header. In this embodiment, an embedded conductor is helically wound around one of the bores 104 into which an end of a therapy lead inserts. The antenna in this instance then acts as a dipole antenna similar to that of FIG. 1A.

Figure 1D:
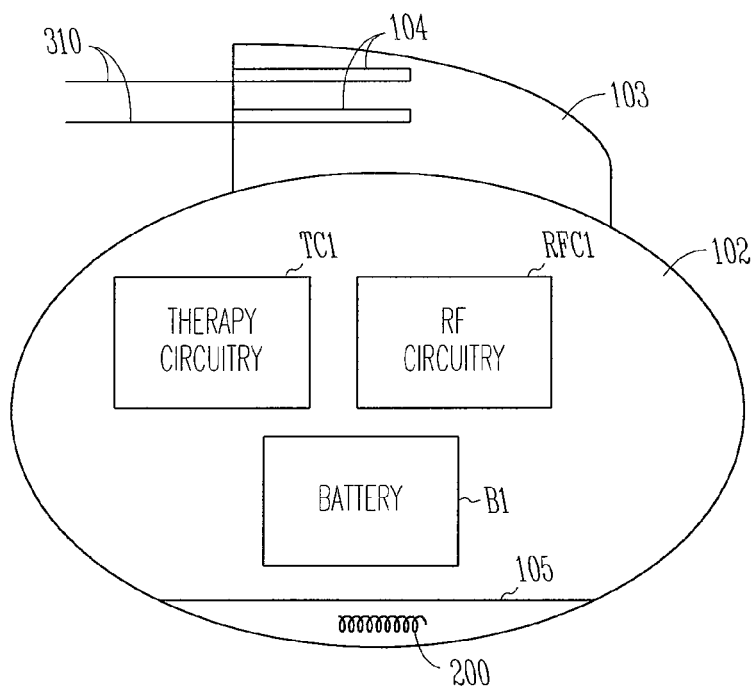

FIG. 1D shows another embodiment where the helical antenna, rather than being located within the header, is embedded within a dielectric pocket 105 adjacent an outer surface of the device housing. The pocket 105 may be constructed of a polymer material similar to that of the header described above and provides similar protective and electrical functions. Again, the size and shape of the device housing is affected minimally, if at all.

In the examples described above, the antenna embedded into either the header or a dielectric pocket was a helical antenna. It should be appreciated, however, that other types of antennas could be similarly embedded, and the same advantages would be obtained.

FIGS. 2A-B and 3A-B are block diagrams of an exemplary implantable cardiac rhythm management device showing examples of how monopole or dipole helical antennas may be connected and driven. In the figures, only one therapy lead 310 is shown but it should be understood that a cardiac rhythm management device may use two or more such leads. A microprocessor controller 302 controls the operation of the therapy circuitry 320, which includes sensing and stimulus generation circuitry that are connected to electrodes by the therapy leads for control of heart rhythm, and RF drive circuitry 330 for transmitting and receiving a carrier signal at a specified frequency modulated with telemetry data. The conductors of the therapy lead 310 connect to the therapy circuitry 320 through a filter 321 that serves to isolate the circuitry 320 from any RF signals that may be picked up by the lead. The filter 321 may be a low-pass filter or a notch filter such as a choke.

The microprocessor 302 also outputs and receives the data contained in the modulated carrier generated or received by the drive circuitry 330. The RF drive circuitry 330 includes an RF transmitter and receiver that are connected by a transmit/receive switch 333 to the antenna. The conductor that connects the transmit/receive switch to the antenna passes from the interior of the device housing to the exterior where the antenna is located through a feedthrough 404. One disadvantage of helical antennas is a relatively narrow bandwidth and low radiation resistance. An antenna tuning circuit may therefore be desirable, and all of the illustrated embodiments employ such a circuit to adjust the impedance of the antenna. An antenna tuning circuit loads the antenna with a variable amount of inductance or capacitance to thereby adjust the effective electrical length of the antenna, and hence the resonance frequency of the antenna. By matching the antenna impedance to the impedance of the transmitter/receiver at a specified carrier frequency, the reactance of the antenna may be tuned out at that frequency so that the antenna forms a resonant structure and efficiently transmits/receives far-field radiation.

Figure 2A:
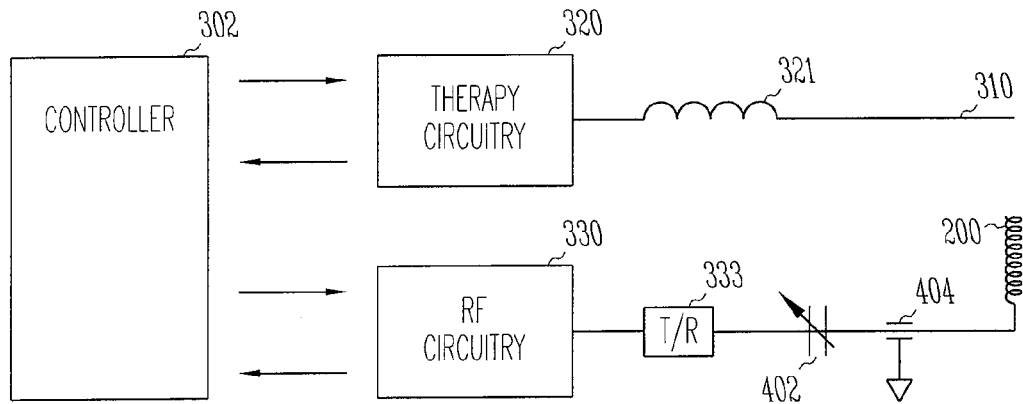
FIGS. 2A and 2B illustrate alternative embodiments for connecting the components of an exemplary cardiac rhythm management device to a helical monopole antenna.
Figure 2B:
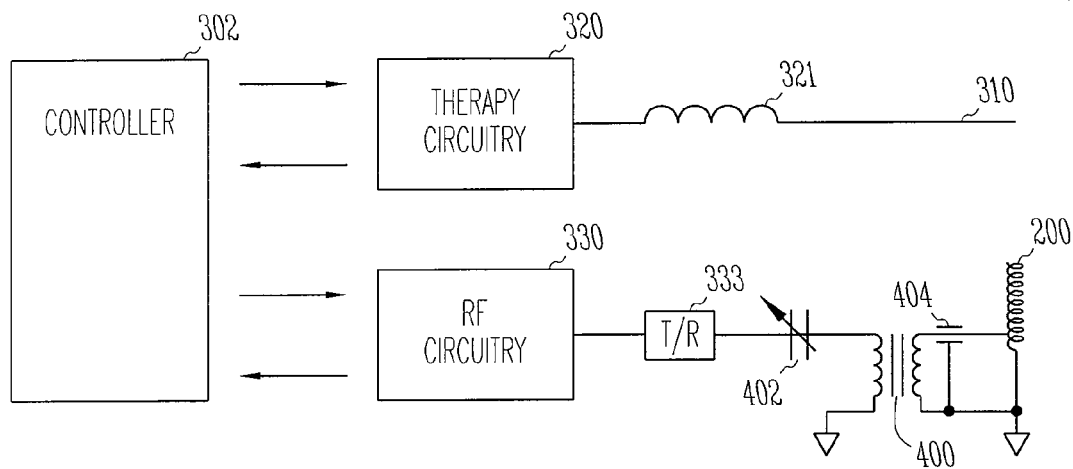

FIGS. 2A and 2B illustrate exemplary methods for connecting and driving helical monopole antennas such as the perpendicularly oriented helix shown in FIG. 1B. In FIG. 2A, the helical antenna 200 is simply connected to the transmit/receive switch 333 through a variable tuning capacitor 402. In FIG. 2B, the antenna is connected to the transmit/receive switch through a balun transformer 400 in addition to the tuning capacitor. The balun transformer allows better impedance matching than when the tuning capacitor alone is used. The driving impedance may also be improved by tapping the antenna 200 in the middle as shown in the figure. The balun transformer also electrically isolates the internal circuitry from the device housing which may be advantageous in some pacemakers and defibrillators where the housing or can is utilized as an electrode in delivering pacing or defibrillation pulses.

Figure 3A:
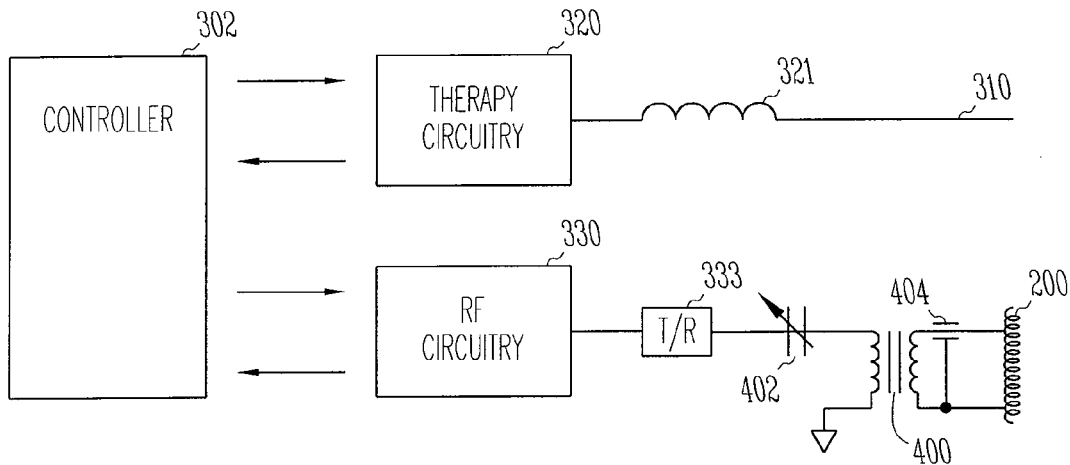
FIGS. 3A and 3B illustrate alternative embodiments for connecting the components of an exemplary cardiac rhythm management device to a helical dipole antenna.
Figure 3B:
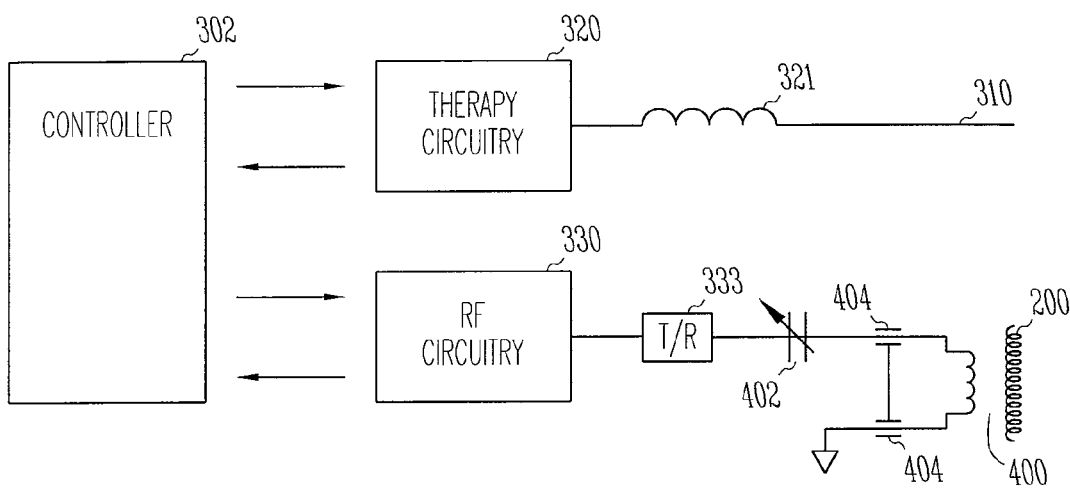

FIGS. 3A and 3B show exemplary methods for connecting and driving helical dipole antennas such as the parallel oriented helices shown in FIGS. 1A, 1C, and 1D. In these embodiments the balun transformer serves to convert the single ended RF signal generated or received by the circuitry into a differential RF signal that is transmitted or received at the antenna in addition to providing improved impedance matching. FIG. 3A shows an embodiment where the balun transformer 400 is interposed between the tuning capacitor and the antenna 200 and also provides electrical isolation. FIG. 3B is an alternative embodiment where the antenna itself serve as one of the windings of the balun transformer 400. This saves space but suffers from a disadvantage that the balun is outside of the housing and hence cannot be used to isolate the internal circuitry from the housing.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable medical device, comprising:
   an implantable medical device housing including an implantable telemetry circuit;
   an implantable helical antenna configured to wirelessly transfer information electromagnetically within a specified operating frequency range, the implantable helical antenna having an axis substantially perpendicular to a ground plane of the implantable helical antenna, the implantable helical antenna having a first end and a second end, wherein the first end is connected to the ground plane and the second end is free-floating; and
   a dielectric member housing the implantable helical antenna, the dielectric member proximate the implantable medical device housing.

2. The implantable medical device of claim 1, wherein the ground plane includes at least a conductive portion of the implantable medical device housing.

3. The implantable medical device of claim 1, wherein the implantable helical antenna is configured to wirelessly transfer information electromagnetically substantially using far-field radiation.

4. The implantable medical device of claim 1, wherein the implantable helical antenna has an effective length corresponding to approximately one-quarter of a wavelength of the specified operating frequency range.

5. The implantable medical device of claim 4, wherein the implantable helical antenna includes a helical conductor having a physical length less than one-quarter of the wavelength of the specified operating frequency range, and the effective length of the implantable helical antenna is longer than the physical length due at least in part to the inductance and capacitance of the helical configuration of the implantable helical antenna.

6. The implantable medical device of claim 1, including a tuning circuit configured to adjust an impedance match between the implantable helical antenna and the implantable telemetry circuit.

7. The implantable medical device of claim 1, wherein the specified operating frequency range includes a frequency range between 300 MHz and 1 GHz.

8. An implantable medical device, comprising:
an implantable medical device housing including an implantable telemetry circuit, wherein a conductive portion of the implantable medical device housing comprises a ground plane;
an implantable helical antenna configured to wirelessly transfer information electromagnetically within a specified operating frequency range, the implantable helical antenna having an axis substantially perpendicular to the ground plane;
a dielectric member housing the implantable helical antenna, the dielectric member proximate the implantable medical device housing;
wherein the implantable helical antenna has an effective length corresponding to approximately one-quarter of a wavelength of the specified operating frequency range, and wherein the implantable helical antenna includes a helical conductor having a physical length less than one-quarter of the wavelength of the specified operating frequency range, the effective length of the implantable helical antenna being longer than the physical length due at least in part to the inductance and capacitance of the helical configuration of the implantable helical antenna.

9. A method, comprising:
using an implantable helical antenna in a dielectric member proximate an implantable medical device housing, the implantable medical device housing including an implantable telemetry circuit; and
wirelessly transferring information electromagnetically within a specified operating frequency range using the implantable helical antenna, the implantable helical antenna having an axis substantially perpendicular to a ground plane, the implantable helical antenna having a first end and a second end, wherein the first end is connected to the ground plane and the second end is free-floating.

10. The method of claim 9, wherein the using the implantable helical antenna having the axis substantially perpendicular to the ground plane includes using an implantable helical antenna having an axis substantially perpendicular to at least a conductive portion of the implantable medical device housing.

11. The method of claim 9, wherein the wirelessly transferring information electromagnetically includes substantially using far-field radiation.

12. The method of claim 9, wherein the using the implantable helical antenna includes using an implantable helical antenna having an effective length corresponding to approximately one-quarter of a wavelength of the specified operating frequency range.

13. The method of claim 12, wherein the using the implantable helical antenna includes using a helical conductor having a physical length less than one-quarter of the wavelength of the specified operating frequency range, the effective length of the implantable helical antenna being longer than the physical length due at least in part to the inductance and capacitance of the helical configuration of the implantable helical antenna.

14. The method of claim 9, including providing a tuning circuit configured to adjust an impedance match between the implantable helical antenna and the implantable telemetry circuit.

* * * * *